US 6,695,777 B2

(12) United States Patent
Solomon et al.

(10) Patent No.: US 6,695,777 B2
(45) Date of Patent: Feb. 24, 2004

(54) METHOD AND APPARATUS FOR ENABLING THE BATTERY PACK SIZE OF AN ULTRASOUND DEVICE TO BE INDEPENDENT OF THE PHYSICAL DESIGN OF THE ULTRASOUND DEVICE

(75) Inventors: Rodney J Solomon, Andover, MA (US); Benjamin M Herrick, Boxboro, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 133 days.

(21) Appl. No.: 09/916,098

(22) Filed: Jul. 26, 2001

(65) Prior Publication Data

US 2003/0022060 A1 Jan. 30, 2003

(51) Int. Cl.[7] .................................................. A61B 8/00
(52) U.S. Cl. ....................................................... 600/437
(58) Field of Search ................................ 600/437, 459; 320/106, 112, 116; 439/247, 500; 429/100, 123

(56) References Cited

U.S. PATENT DOCUMENTS

| 5,149,603 | A | * | 9/1992 | Fleming et al. ................. 429/98 |
| 5,212,021 | A | * | 5/1993 | Smith et al. ..................... 429/9 |
| 5,295,485 | A | * | 3/1994 | Shinomura et al. .......... 600/443 |
| 5,850,134 | A | * | 12/1998 | Oh et al. ...................... 320/106 |
| 5,931,791 | A | * | 8/1999 | Saltzstein et al. ............ 600/513 |
| 6,249,105 | B1 | * | 6/2001 | Andrews et al. ............. 320/106 |
| 6,403,254 | B1 | * | 6/2002 | Wang ............................ 429/123 |

* cited by examiner

Primary Examiner—Francis J. Jaworski
(74) Attorney, Agent, or Firm—John Vodopia

(57) ABSTRACT

A method and apparatus are provided for enabling battery packs of different sizes to be used with an ultrasound device. The apparatus of the present invention comprises an ultrasound device having a battery pack installment apparatus configured to be capable of being coupled with battery packs of different sizes. The method comprises the step of providing the ultrasound device with a battery pack installment apparatus that is configured to couple with battery packs of different sizes.

13 Claims, 2 Drawing Sheets

METHOD AND APPARATUS FOR ENABLING THE BATTERY PACK SIZE OF AN ULTRASOUND DEVICE TO BE INDEPENDENT OF THE PHYSICAL DESIGN OF THE ULTRASOUND DEVICE

TECHNICAL FIELD OF THE INVENTION

The present invention relates to ultrasound devices and, more particularly, to a method and apparatus that enables battery packs of different sizes to be used with an ultrasound device.

BACKGROUND OF THE INVENTION

An ongoing effort is being made by manufacturers of medical ultrasound imaging systems to make them small and portable so that clinicians can easily carry them to the patient location. This is viewed in the ultrasound industry as a superior alternative in many situations to the conventional approach of having a large, expensive and immobile ultrasound system located in an examination room.

Currently, portable ultrasound systems are available that are capable of being powered by a battery pack that is attached by some mechanism to the ultrasound device. For example, SonoSite, Inc. of Bothell, Wash. provides a small, battery-powered, portable medical ultrasound imaging system that is powered by a rechargeable 3.0 ampere hour battery that is located inside the ultrasound system and that is easily removable. The ultrasound system can operate for 1.5 to 4 hours on a charged battery. The battery is designed to be removable so that a discharged battery can be removed and a fully charged battery can be installed. The ultrasound system can then be used while the discharged battery is being recharged.

One of the disadvantages of this type of solution is that, because the battery packs are installed either in a compartment within the ultrasound system or within a recessed region of the ultrasound system, a larger battery pack or a battery pack having a slightly different form factor cannot be used with the ultrasound system. In other words, the physical structure of the ultrasound system, or at least the mechanisms for securing the battery pack to the ultrasound system, would have to be altered to accommodate the change in the battery pack.

Accordingly, a need exists for a method and apparatus that would enable battery packs of different sizes and/or that have different form factors to be used with an ultrasound device without having to change the physical structure of the ultrasound device to accommodate the change in the battery pack and without having to change the mechanism for securing the battery pack to the ultrasound device.

SUMMARY OF THE INVENTION

A method and apparatus for enabling battery packs of different sizes to be used with an ultrasound device. The apparatus of the present invention comprises an ultrasound device having a battery pack installment apparatus configured to be capable of being coupled with battery packs of different sizes. The method comprises the step of providing the ultrasound device with a battery pack installment apparatus that is configured to couple with battery packs of different sizes.

These and other features and advantages of the present invention will become apparent from the following description, drawings and claims.

DETAILED DESCRIPTION OF THE INVENTION

Figure 2:
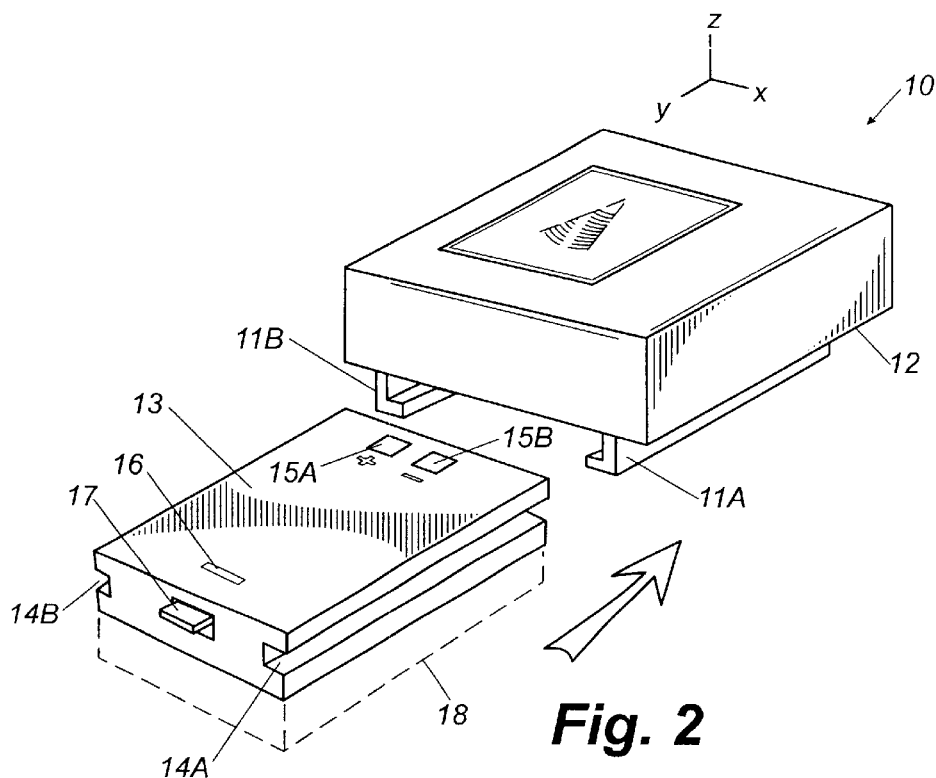
FIG. 2 is a pictorial representation of an ultrasound device that can be used with a battery pack of various sizes and/or form factors in accordance with another example embodiment without having to change the physical structure of the ultrasound device or the mechanism for securing the battery pack to the ultrasound device to accommodate a change in the size and/or form factor of the battery pack.
Figure 3:
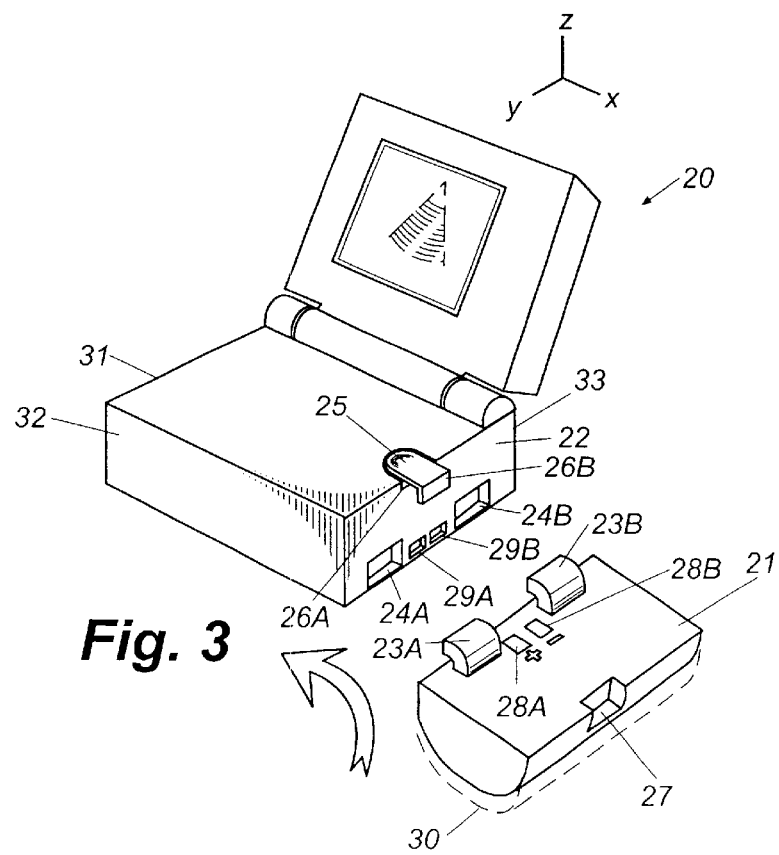
FIG. 3 is a pictorial representation of an ultrasound device that can be used with a battery pack of various sizes and/or form factors in accordance with another example embodiment without having to change the physical structure of the ultrasound device or the mechanism for securing the battery pack to the ultrasound device to accommodate a change in the size and/or form factor of the battery pack.

The present invention enables an ultrasound device to be used with battery packs of various sizes and/or form factors without having to change the physical structure of the ultrasound device or the mechanism(s) used to secure the battery pack to the ultrasound device. Since the present invention is not limited to any particular ultrasound device design, battery pack design, or mechanisms for securing the battery packs to the ultrasound devices, three different examples that demonstrate the overall concept of the present invention and the manner in which this concept can be implemented are illustrated in FIGS. 1–3.

However, these examples are merely demonstrative of the various manners in which the concepts of the present invention can be implemented and are not intended to represent the only embodiments of the present invention. Those skilled in the art will understand, in view of the discussion provided herein, that there are an infinite number of ways in which the size of a battery pack can be made independent of the physical design of the ultrasound device with which it is used. Multiple examples of ultrasound device designs and battery pack designs, as well as the associated battery pack securing apparatus of the ultrasound device and the coupling mechanism of the battery pack, will be given to demonstrate examples of the ways that ultrasound device designs, battery pack designs, ultrasound device battery pack securing apparatus designs and battery pack coupling mechanism designs can be created or selected to achieve the goals of the invention.

Figure 1:
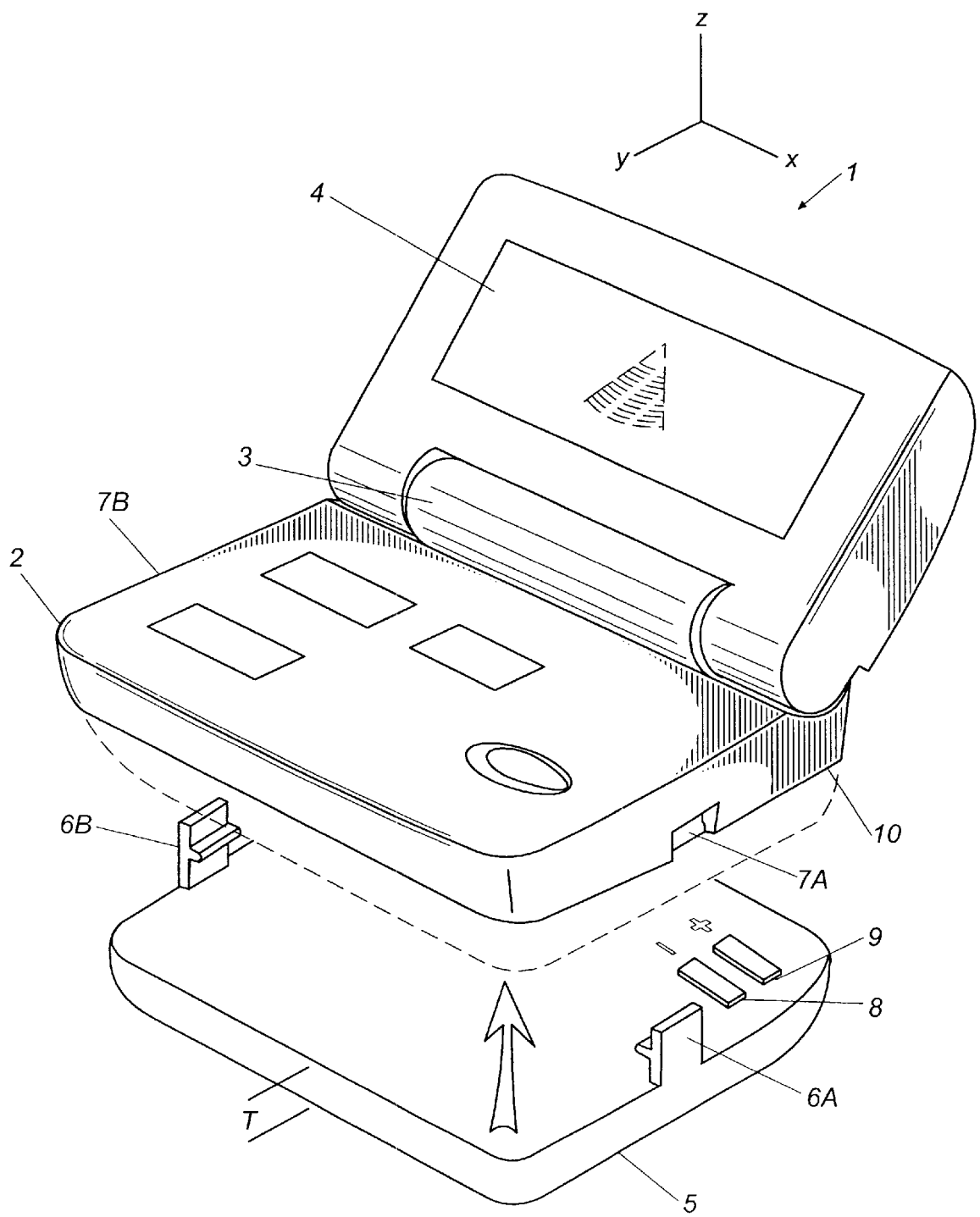
FIG. 1 is a pictorial representation of an ultrasound device that can be used with a battery pack of various sizes and/or form factors in accordance with one example embodiment without having to change the physical structure of the ultrasound device or the mechanism for securing the battery pack to the ultrasound device to accommodate a change in the size and/or form factor of the battery pack.

FIG. 1 is a perspective, pictorial representation of an ultrasound device 1 that is portable, capable of being battery powered and that has a design that is similar to a typical laptop computer. The ultrasound device 1 has a control panel 2, a display monitor 4 and a hinging mechanism 3 that enables the display monitor 4 to be rotated in the y-direction toward and away from the control panel 2 to open, close and adjust the positioning of the display monitor 4. The bottom surface 10 of the ultrasound device has negative and positive contact terminals (not shown) that are positioned to be in contact with negative and positive contact terminals 8 and 9, respectively, of a rechargeable battery pack 5 when the battery pack 5 is secured to the ultrasound device via latches 6A and 6B that interlock with latching receptacles 7A and 7B, respectively. Latching receptacle 7B cannot be seen in the view shown in FIG. 1, but it is identical to latching receptacle 7A. The dashed lines along the bottom surface 10 of the ultrasound device 1 represent the battery pack 5 when it is secured to the bottom surface 10 of the ultrasound device 1.

The size of the battery pack 5 could be increased in a number of ways without having to alter the physical structure of the ultrasound device 1 and without having to alter the designs of the mechanisms 6A, 6B, 7A and 7B used to secure the battery pack 5 to the ultrasound device 1. For example, the battery pack 5 has a thickness, T, in the z-direction and this thickness is generally proportional to the amount of time that the battery pack 5 will power the ultrasound device before having to be recharged. If the battery pack 5 were made larger by increasing its thickness, T, in the downward z-direction, the battery pack would power the ultrasound device 1 for an even longer period of time before needing to be recharged. It is apparent from FIG. 1 that the thickness of the battery pack 5 could be increased and that neither the physical structure of the ultrasound device 1 nor the design or structure of the securing mechanisms 6A, 6B, 7A, and 7B would need to be changed.

It should be noted that, rather than changing the entire thickness, T, of the battery pack 5 in the downward z-direction, the thickness T of a certain portion, or portions, of the battery pack 5 could be increased in the downward z-direction without having to change the physical structure of the ultrasound device 1 or the design or structure of the securing mechanisms 6A, 6B, 7A, and 7B to accommodate the change in the thickness of the battery pack 5. Of course, the battery pack 5 could also be decreased in thickness without having to change the physical structure of the ultrasound device 1 or the design or structure of the securing mechanisms 6A, 6B, 7A, and 7B to accommodate the change in the thickness of the battery pack 5.

It should also be noted that the width (y-direction) and/or length (x-direction) of the battery pack 5 could also be altered without having to change the physical structure of the ultrasound device 1 or the design or structure of the securing mechanisms 6A, 6B, 7A, and 7B to accommodate the change in the thickness of the battery pack 5. However, in these cases, it would be necessary to ensure that the latching mechanisms 6A and 6B remain at their respective x, y coordinate locations so that they will remain aligned with the latching receptacles 7A and 7B. The securing mechanisms 6A and 6B correspond to one example of a suitable design for the battery pack coupling mechanism. The securing mechanisms 7A and 7B correspond to one example of a suitable design for the ultrasound device battery pack securing apparatus.

Practical reasons exist for wanting to be able to enable a portable ultrasound device to be capable of being equipped with battery packs of different sizes (and thus of different ampere hours). One reason is that this allows the size and weight of the ultrasound device to be tailored to the application. For example, if the ultrasound device is likely to sit in a charging cradle in a doctor's office the majority of the time and only be used intermittently for short periods of time, the battery pack size can be relatively small. On the other hand, if the ultrasound device is intended to be used by a healthcare worker doing rounds in a hospital for relatively long periods of time, it would be desirable to use a battery pack of a larger size to eliminate the need to recharge the battery during rounds. In all of these cases, an ultrasound device having a particular physical structure or design could be equipped with different size batteries depending on the manner in which the ultrasound device is going to be used.

FIG. 2 is a pictorial representation of an ultrasound device that can be used with a battery pack of various sizes and/or form factors in accordance with another example embodiment without having to change the physical structure of the ultrasound device or the mechanism for securing the battery pack to the ultrasound device to accommodate a change in the size and/or form factor of the battery pack. In this example, the ultrasound device 10 has rails 11A and 11B located on the bottom surface 12 of the ultrasound device 10. A rechargeable, removable battery pack 13 has grooves 14A and 14B formed in the sides of the battery pack 13 that are shaped to slidably engage rails 11A and 11B so that the battery pack 13 can be fully inserted into the ultrasound device 10 in the y-direction. When the battery pack 13 is fully inserted into the ultrasound device 10 in the y-direction, the positive and negative electrical contacts 15A and 15B will be in contact with positive and negative electrical contacts (not shown) disposed on the bottom surface 12 of the ultrasound device 10.

When the battery pack 13 is in its fully-installed position, an upwardly projecting latch 16 is received in a receptacle (not shown) located on the bottom surface 12 of the ultrasound device 10. The interlocking of the latch 16 and the receptacle (not shown) prevents the battery pack 13 from moving in the y-directions. In order to remove the battery pack 13, a tab 17 is pushed in the downward z-direction, thereby causing the latch 16 to move in the downward z-direction so that it is no longer engaged in the receptacle located on the bottom surface of the ultrasound device 10. The battery pack 13 can then be removed from the ultrasound device 10 by sliding the battery pack in the rearward y-direction.

The dashed box 18 indicates how the thickness of the battery pack 13 can be increased in the downward z-direction without having to alter the physical structure or design of the ultrasound device and without having to alter the engagement/securing mechanisms 11A, 11B, 14A, 14B 16 and 17. Of course, the battery pack could be decreased in thickness in a similar manner.

FIG. 3 is a pictorial representation of an ultrasound device that can be used with a battery pack of various sizes and/or form factors in accordance with another example embodiment without having to change the physical structure of the ultrasound device or the mechanism for securing the battery pack to the ultrasound device to accommodate a change in the size and/or form factor of the battery pack. In accordance with this embodiment, the ultrasound device 20 has a laptop computer design similar to that shown in FIG. 1. However, in this embodiment, the rechargeable battery pack 21 is removably securable to the side 22 of the ultrasound device 20. The battery pack 21 has clips 23A and 23B on it that are shaped and adapted to be engaged by receptacles 24A and 24B, respectively. When the clips 23A and 23B are engaged in the receptacles 24A and 24B, the battery pack 21 is rotated upwards in the z-direction and forward in the x-direction until the downward projecting walls 26A and 26B of the latch 25 grasp a recess in the cutaway area 27 of the battery pack 21. The latch 25 comprises a pivot mechanism (not shown) such that pressure placed on the rear portion of the latch (i.e., the end opposite the end comprising wall 26B) in the downward z-direction causes walls 26A and 26B to move in the upward z-direction. The latch 25 is spring-loaded so that it is biased to its closed position, thus preventing the battery pack 21 from being unintentionally separated from the ultrasound device 20.

In the installed position, the positive and negative electrical contacts 28A and 28B on the battery pack 21 are in contact with the positive and negative electrical contacts 29A and 29B on the side 22 of the ultrasound device 20. This is also the case with the designs shown in FIGS. 1 and 2. In these cases, preferably protection (not shown) is provided about each contact of the ultrasound device and about each contact of the battery pack to prevent short circuits from occurring between the contacts.

It should be noted that it is not necessary that installation result in enabling power to be supplied from the battery pack to the ultrasound device. This is true regardless of the shape and design of the battery pack and the ultrasound device with which it is used. For example, once the battery pack is installed, electrical connection between the battery pack and the ultrasound device can be accomplished in some other way, such as, for example, by connecting the battery pack to the ultrasound device via a wire and plug arrangement that enables power to be supplied from the battery pack to the ultrasound device.

The latching configuration is sufficient to maintain the battery pack 21 in its installed position until a force is applied to the rear portion of the latch 25 (i.e., the end of the latch 25 opposite the end of the latch having wall 26B extending therefrom) in the downward z-direction. When such a force is applied, the battery pack 21 can be rotated away from the ultrasound device, thereby disengaging the clips 23A and 23B from the receptacles 24A and 24B. The dashed lines 30 mirroring the shape of the battery pack 21 are intended to indicate that the dimensions of the battery pack 21 can be increased or decreased in shape without having to change the physical structure of the ultrasound device 20 or the mechanisms 23A, 23B, 24A, 24B, 25, 26A, 26B or 27 that are used to secure the battery pack 21 to the ultrasound device 20. It should also be noted that the configuration of the side 22 of the ultrasound device 20 could alternatively be located on one of the other sides 31, 32 or 33 of the ultrasound device 20 and that the battery pack 21 could installed on one of those sides rather than on side 22 of the ultrasound device.

It should be noted that the present invention has been described with reference to example embodiments and that the present invention is not limited these example embodiments. Multiple examples of ultrasound device designs and battery pack designs, as well as the associated battery pack securing apparatus of the ultrasound device and the coupling mechanism of the battery pack, have been given simply to demonstrate that virtually an infinite number of ultrasound device designs, battery pack designs, ultrasound device battery pack securing apparatus designs and battery pack coupling mechanism designs can be created or selected to achieve the goals of the invention. With respect to a given ultrasound device, multiple variations in the dimensions of the battery pack can be made without having to alter the physical design of the ultrasound device or the physical designs of the associated battery pack securing apparatus of the ultrasound device and the coupling mechanism of the battery pack. Therefore, those skilled in the art will understand from the discussion provided herein that there are many ways of achieving the goals of the present invention without deviating from the scope of the present invention.

What is claimed is:

1. An ultrasound device, the ultrasound device comprising:
   a battery pack installment apparatus having at least one battery coupling mechanism, the battery pack installment apparatus being configured to be capable of being coupled with a first battery pack and a second battery pack, said first and second battery packs having different dimensions in at least two of the x-, y- and z-axes, such as the first battery pack having a first measurable dimension in the x-axis and a second measurable dimension in the y-axis, and the second battery pack having a significantly larger measurable dimension than the first measurable dimension towards the positive and/or towards the negative direction of the x-axis and a significantly larger measurable dimension than the second measurable dimension towards the positive and/or towards the negative direction of the y-axis without changing the physical structure of the ultrasound device or the design or structure of the at least one battery coupling mechanism for accommodating the change in the first and second measurable dimensions.

2. The ultrasound device of claim 1, wherein the battery pack installment apparatus is configured to be capable of being removably coupled with the coupling mechanism of each battery pack.

3. The ultrasound device of claim 1, wherein the battery pack installment apparatus is configured to be capable of being coupled with a coupling mechanism of each battery pack via a latching mechanism.

4. The ultrasound device of claim 1, wherein the battery pack installment apparatus is configured to be capable of being coupled with a coupling mechanism of each battery pack via sliding engagement.

5. The ultrasound device of claim 1, wherein the battery pack installment apparatus is configured to be capable of being coupled with a coupling mechanism of each battery pack via a hinging and latching mechanism.

6. The ultrasound device of claim 1, wherein the ultrasound device comprises electrical contacts that are in abutment with respective electrical contacts of the battery pack when the battery pack is coupled with the battery pack installment apparatus of the ultrasound device such that power is capable of being supplied by the battery pack to the ultrasound device via abutment of the electrical contacts of the ultrasound device with the respective electrical contacts of the battery pack.

7. The ultrasound device of claim 1, wherein when the battery pack is coupled with the battery pack installment apparatus of the ultrasound device, power is capable of being supplied by the battery pack to the ultrasound device via and electrical cable that electrically couples the ultrasound device to the battery pack.

8. The ultrasound device of claim 1, wherein the battery pack installment apparatus is configured to be capable of being removably coupled with a coupling mechanism of each battery pack via a latching mechanism.

9. The ultrasound device of claim 1, wherein the battery pack installment apparatus is configured to be capable of being removably coupled with a coupling mechanism of each battery pack via sliding engagement.

10. The ultrasound device of claim 1, wherein the battery pack installment apparatus is configured to be capable of being removably coupled with a coupling mechanism of each battery pack via a hinging and latching mechanism.

11. A method for adapting an ultrasound device to be capable of being equipped with battery packs of different sizes, the method comprising the step of:
   providing the ultrasound device with a battery pack installment apparatus having at least one battery coupling mechanism, the battery pack installment apparatus is configured to couple with a first battery pack and a second battery pack, said first and second battery packs having different dimensions in at least two of the x-, y- and z-axes, such as the first battery pack having a first measurable dimension in the x-axis and a second measurable dimension in the y-axis, and the second battery pack having a significantly larger measurable dimension than the first measurable dimension towards the positive and/or towards the negative direction of the x-axis and a significantly larger measurable dimension than the second measurable dimension towards the positive and/or towards the negative direction of the y-axis without changing the physical structure of the ultrasound device or the design or structure of the at least one battery coupling mechanism for accommodating the change in the first and second measurable dimensions.

12. The method of claim 11, wherein the method further comprises the step of:
   providing battery packs of different sizes with coupling mechanisms that are configured to be capable of coupling with the battery pack installment apparatus of the ultrasound device.

13. The method of claim 12, wherein the coupling mechanisms of said battery packs of different sizes are at least substantially identical in size and structure.

* * * * *